United States Patent [19]

Luce

[11] Patent Number: 5,754,273
[45] Date of Patent: May 19, 1998

[54] NON-CONTACT TONOMETER HAVING OFF-AXIS FLUID PULSE SYSTEM

[75] Inventor: David A. Luce, Clarence Center, N.Y.

[73] Assignee: Leica Inc., Depew, N.Y.

[21] Appl. No.: 804,004

[22] Filed: Feb. 21, 1997

[51] Int. Cl.⁶ .................................................. A61B 3/10
[52] U.S. Cl. ........................ 351/212; 351/208; 600/401
[58] Field of Search ................................. 351/205, 208,
351/212, 247; 128/648, 652; 600/401, 405

[56] References Cited

U.S. PATENT DOCUMENTS 4,834,527  5/1989  Kobayaski ............................... 351/208
4,881,807  11/1989  Luce et al. ............................... 351/208

*Primary Examiner*—Huy Mai
*Attorney, Agent, or Firm*—Bean, Kauffman & Snyder

[57] ABSTRACT

A non-contact tonometer includes a fixation axis intersecting the corneal vertex, and a fluid axis angularly displaced from the fixation axis to form a non-zero angle therewith. A nozzle is axially aligned along the fluid axis for discharging a fluid pulse along the fluid axis to the corneal surface of the eye. In a preferred embodiment, the fixation and fluid axes reside in the same vertical plane, with the fluid axis below the fixation axis approaching the eye. Alignment and applanation detection optics are arranged coplanar with the fluid axis.

10 Claims, 2 Drawing Sheets

NON-CONTACT TONOMETER HAVING OFF-AXIS FLUID PULSE SYSTEM

BACKGROUND OF THE INVENTION

A. Field of the Invention

The present invention relates generally to ophthalmic instruments, and more particularly to a non-contact tonometer for measuring intraocular pressure (IOP) having a fluid axis which is angularly displaced from a fixation axis of the instrument.

B. Description of the Prior Art

Non-contact tonometers for measuring IOP have been constructed for over twenty-five years to operate by forcing a fluid, such as air, through a discharge nozzle toward a cornea of a patient to flatten the cornea, a condition known in the art as applanation. The fluid impulse necessary to cause applanation is monitored and correlated to IOP. In all prior art non-contact tonometers, the fluid discharge nozzle defines a fluid axis which coincides with a fixation axis of the instrument. When a prior art instrument of this type is properly aligned, the patient is fixated upon a target presented along the fixation axis, and the fluid pulse is directed along the coincident fluid and fixation axes toward the corneal vertex normal to the corneal surface. The moment of applanation is determined by detecting a peak of reflected light from the flattened corneal surface.

While it is commonplace for an individual being tested to blink in response to the fluid pulse, blink response time is on the order of 100 milliseconds, far slower than the 5 milliseconds required for measurement of even the highest IOPs, and thus the eyelid typically does not interfere with IOP measurement. However, clinical observers have found that in testing some individuals who naturally carry their eyelids substantially lower than a majority of the population, it is often necessary to manually raise the eyelid to prevent the eyelid from interfering with IOP measurement. Also, an inadvertent blink by the patient just prior to the fluid pulse may interfere with IOP measurement.

Another problem become increasingly prevalent in the field of non-contact tonometry involves the testing of individuals who have previously undergone a corrective procedure known as photo-refractive keratotomy (PRK). In this procedure, surface layers of corneal tissue are removed from a central region of the cornea approximately 3 mm in diameter. The remaining corneal tissue in the surgically altered region is relatively rough compared to the natural surface tissue, and consequently exhibits unpredictable reflective characteristics which may render the reflection-based applanation detection system inoperative for prior art tonometers having coincident fluid and fixation axes incident upon the altered central region.

SUMMARY OF THE INVENTION

Therefore, it is an object of the present invention to provide a non-contact tonometer which avoids the need to manually relocate a patient's upper eyelid for testing purposes in situations where the patient's eyelid is naturally in a position which would cause it to interfere with a fluid pulse directed along coincident fluid and fixation axes.

It is another object of the present invention to provide a non-contact tonometer which does not cause applanation of a surgically altered central region of the cornea in patients who have undergone PRK.

In furtherance of these and other objects, a non-contact tonometer of the present invention includes a fixation axis having a fixation target presented therealong for fixing the gaze of the eye in the direction of the fixation axis, and a fluid axis forming a non-zero angle with the fixation axis. In a preferred embodiment, the fixation and fluid axes reside in a substantially vertical plane, with the fluid axis approaching the eye from below the fixation axis. Optical alignment means is provided for positioning the fluid axis normal to the corneal surface, and applanation detection means is provided for determining the condition of applanation caused by a fluid pulse.

BRIEF DESCRIPTION OF THE DRAWINGS

The nature and mode of operation of the present invention will now be more fully described in the following detailed description of a preferred embodiment taken with the accompanying drawing figures, in which.

DETAILED DESCRIPTION OF THE PREFERRED EMBODIMENT

Figure 1:
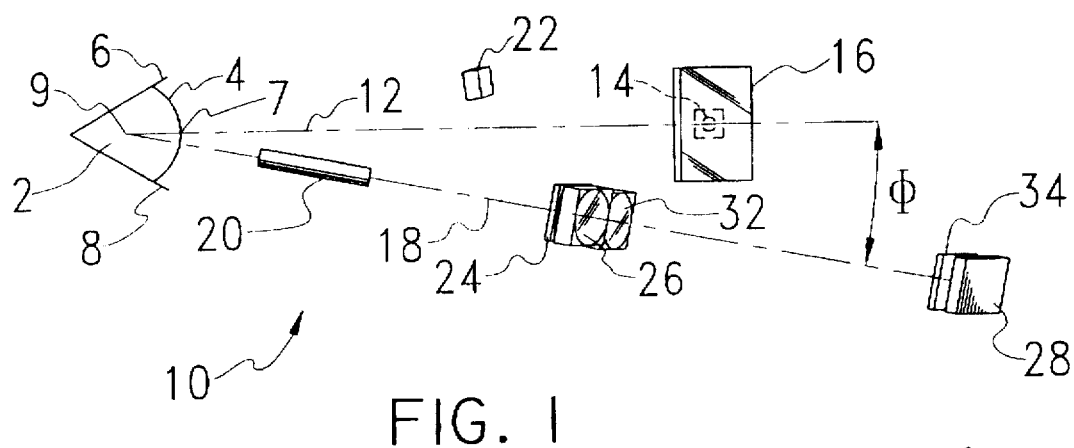
FIG. 1 is a schematic side elevational view of a non-contact tonometer formed in accordance with a preferred embodiment of the present invention.
Figure 2:
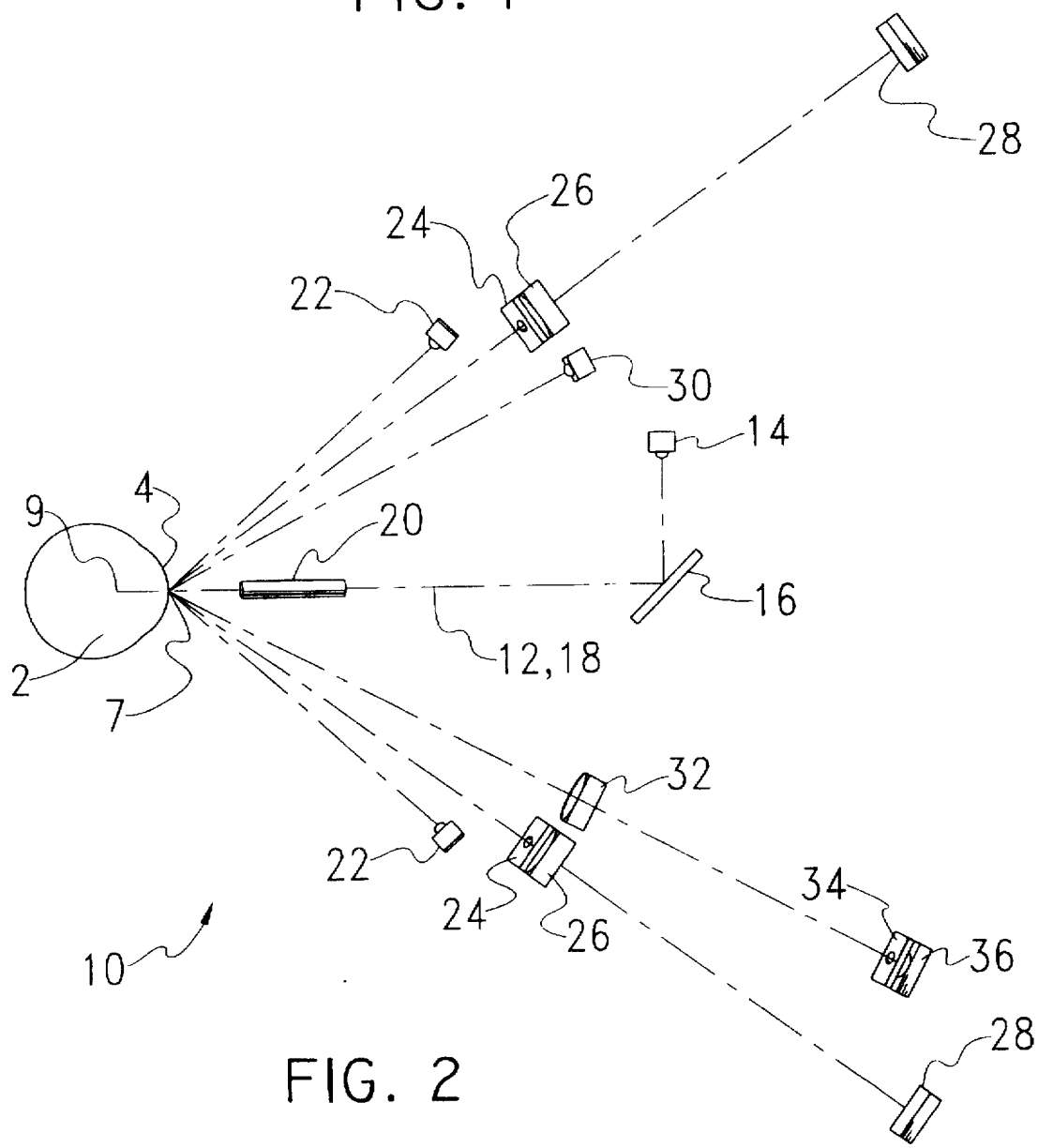
FIG. 2 is a schematic top plan thereof.

Referring to both FIGS. 1 and 2, a non-contact tonometer generally designated as 10 is shown schematically in an aligned position relative to an eye 2 for measuring IOP. Eye 2 is fixated on target light presented along a fixation axis 12 by a beam splitter 16 centered on the fixation axis which redirects light from a target light source 14 located remotely of the fixation axis, as is well-known in the art of tonometry. As will be understood from the drawing figures, fixation axis 12 intersects corneal surface 4 at the corneal vertex 7.

Tonometer 10 further includes fluid discharge means in the form of a nozzle 20 which defines a fluid axis 18 along which a fluid pulse travels to reach corneal surface 4. Nozzle 20 communicates in a conventional manner with air pulse generation means, such as a piston mechanism, not shown. As best seen in FIG. 1, fluid axis 18 forms a non-zero angle $\Phi$ with fixation axis 12, with a vertex located at the center of curvature 9 of corneal surface 4. In a preferred embodiment, fluid axis 18 is situated in the same vertical plane as fixation axis 12, and is below the fixation axis approaching eye 2. Non-zero angle $\Phi$ is desirably between 10 and 15 degrees, and most desirably 11 degrees, so as to move the point of incidence of the air pulse on corneal surface 4 further away from upper eyelid 6 relative to prior art tonometers, without involving lower eyelid 8, and without need to applanate a surgically altered corneal region in a PRK patient. Since the pressure of the fluid contained within the anterior chamber of the eye is the same at all points (neglecting the very slight effects of gravity), IOP measurement is not changed by varying the point of incidence of the fluid pulse. Moreover, lower eyelid 8 is not prone to significant movement which would hamper or interfere with testing.

Figure 3:
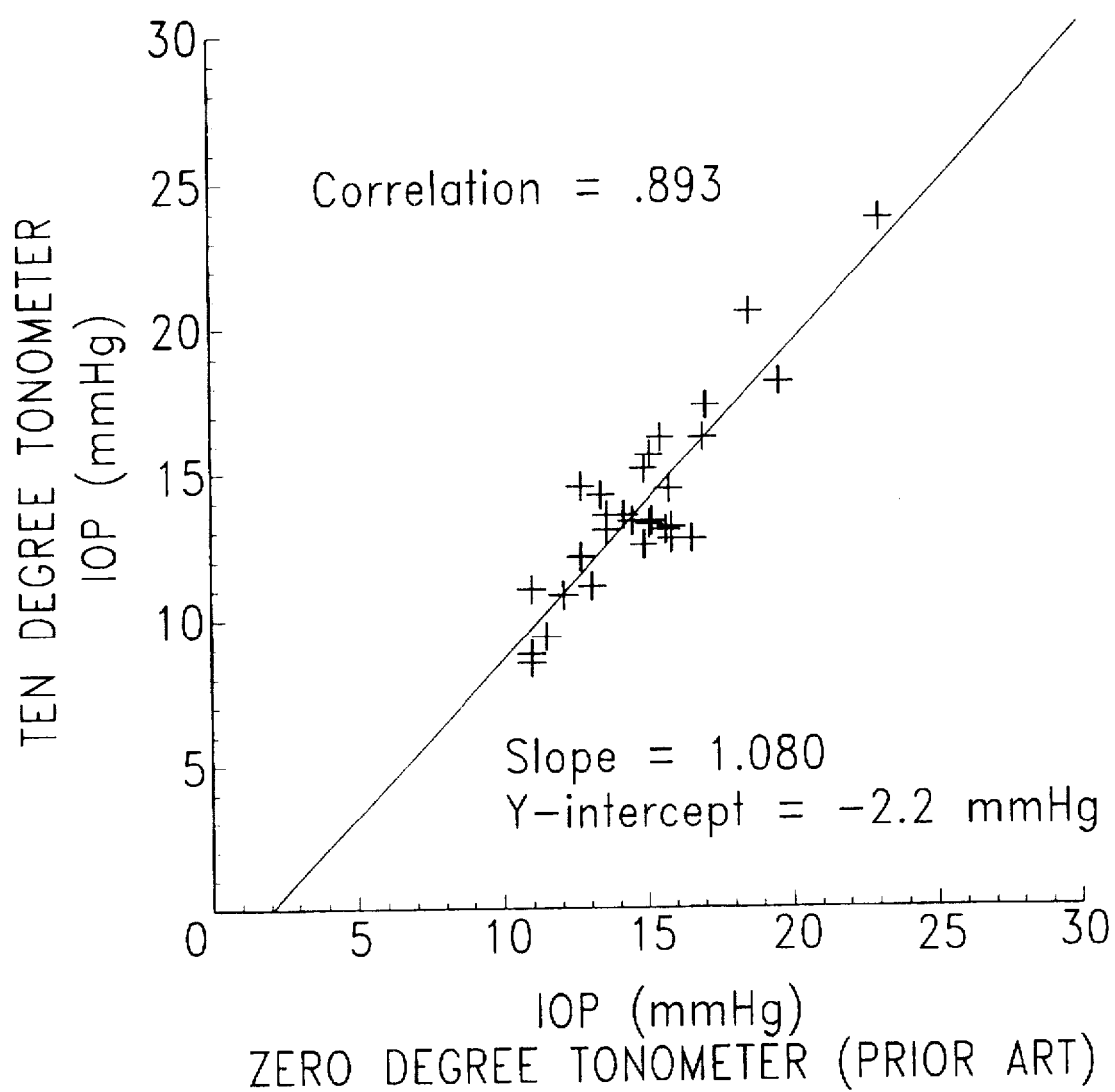
FIG. 3 is a graph of average IOP measurements taken using an "off-axis" tonometer formed in accordance with the present invention against average IOP measurements for the same test subjects taken using a "straight ahead" tonometer of the prior art.

Initial micro-clinical trials have demonstrated the utility of the present invention. FIG. 3 is a graphical representation showing the results of a micro-clinical trial in which twenty-nine eyes of fifteen test subjects were tested with a prior art non-contact tonometer having coincident (zero-degree angle) fluid and fixation axes, and also with a non-contact tonometer of the present invention having a fluid axis forming a ten-degree angle with a fixation axis thereof. A total of six measurements were made for each eye, three measurements with the zero-degree instrument of the prior art and three measurements with the ten-degree instrument of the present invention. The averages of each set of three measurements are plotted against each other in FIG. 3. The average standard deviation for twenty-nine sets of three measurements was 0.9 mmHg for both instruments, an indication that increased measurement spread within sets of three readings is not a concern with regard to the present invention. A correlation coefficient of 0.893 was found between the measurements of the two instruments.

As in prior art non-contact tonometers, the fluid axis 18 must be aligned to intersect the eye normal to corneal surface 4. A number of optical alignment systems have heretofore been proposed, and the current invention may be practiced utilizing an optical alignment system disclosed in commonly-owned U.S. Pat. No. 4,881,807 issued Nov. 21, 1989, the disclosure of which is incorporated herein by reference. A possible alignment system is shown in FIGS. 1 and 2 herein as including a pair of opposite light sources 22 symmetrically arranged about fixation axis 12 and fluid axis 18 for illuminating the eye with rays of light, and corresponding symmetric pin-hole occluders 24, lenses 26, and area detectors 28 for receiving a small bundle of rays reflected by corneal surface 4. Elements cooperating for the detection of corneally reflected rays, namely occluders 24, lenses 26, and area detectors 28, are arranged to be coplanar with fluid axis 18 to permit alignment of the fluid axis normal to corneal surface 4. As described in the referenced patent, the alignment system may provide a visual instruction to the practitioner for manual positioning of the test portion of the instrument, or it may provide signal information to automatic means for positioning the test portion of the instrument.

A conventional applanation detection system is also provided, but like the chosen alignment system, it is arranged to accommodate for the novel angular orientation of fluid axis 18 relative to fixation axis 12. The applanation detection system includes an emitter 30 on one side of fluid axis 18, and a lens 32, a pin-hole occluder 34, and a photo-detector 36 on the opposite side of fluid axis 18. Emitter 30, photo-detector 32, occluder 34, and photo-detector 36 are preferably aligned in a common plane with fluid axis 18, such that when flattening of corneal surface 4 occurs in response to a fluid pulse, a peak flux is detected by photo-detector 32 in a known manner. A suitable applanation detection system is currently used in the XPERT® NCT manufactured by Reichert Ophthalmic Instruments.

What is claimed is:

1. A non-contact tonometer comprising:

a fixation axis;

a fixation target presented along said fixation axis;

a fluid axis forming a non-zero angle with said fixation axis; and discharge means arranged for delivering a fluid pulse along said fluid axis to a corneal surface of an eye fixated on said fixation target.

2. The tonometer according to claim 1, further including optical alignment means for aligning said fluid axis normal to said corneal surface.

3. The tonometer according to claim 2, wherein said optical alignment means includes light source means for illuminating the eye with light rays and detector means for receiving a small bundle of rays reflected by said corneal surface, and said detector means is coplanar with said fluid axis.

4. The tonometer according to claim 1, further including applanation detection means for monitoring deformation of said corneal surface.

5. The tonometer according to claim 4, wherein said applanation detection means is coplanar with said fluid axis.

6. The tonometer according to claim 1, wherein said fixation axis and said fluid axis are coplanar.

7. The tonometer according to claim 6, wherein said fixation axis and said fluid axis reside in a substantially vertical plane.

8. The tonometer according to claim 7, wherein said fluid axis is below said fixation axis.

9. The ophthalmic instrument according to claim 8 wherein said non-zero angle is between 10 and 15 degrees.

10. The ophthalmic instrument according to claim 9 wherein said non-zero angle is approximately 11 degrees.

* * * * *